(12) United States Patent
Yu

(10) Patent No.: US 9,393,035 B2
(45) Date of Patent: Jul. 19, 2016

(54) SYSTEMS AND METHODS FOR RESTORING BLOOD FLOW TO A VESSEL

(71) Applicant: Yongyi Alan Yu, Maple Grove, MN (US)

(72) Inventor: Yongyi Alan Yu, Maple Grove, MN (US)

( * ) Notice: Subject to any disclaimer, the term of this patent is extended or adjusted under 35 U.S.C. 154(b) by 0 days.

(21) Appl. No.: 14/768,920

(22) PCT Filed: Apr. 12, 2014

(86) PCT No.: PCT/US2014/033891
§ 371 (c)(1),
(2) Date: Aug. 19, 2015

(87) PCT Pub. No.: WO2014/169266
PCT Pub. Date: Oct. 16, 2014

(65) Prior Publication Data
US 2016/0000450 A1    Jan. 7, 2016

Related U.S. Application Data

(60) Provisional application No. 61/811,689, filed on Apr. 12, 2013.

(51) Int. Cl.
| | |
|---|---|
| *A61B 17/22* | (2006.01) |
| *A61B 17/221* | (2006.01) |
| *B23K 26/38* | (2014.01) |
| *B23K 26/40* | (2014.01) |
| *A61B 17/00* | (2006.01) |

(52) U.S. Cl.
CPC ............... *A61B 17/221* (2013.01); *B23K 26/38* (2013.01); *B23K 26/40* (2013.01); *A61B 2017/00867* (2013.01); *A61B 2017/00893* (2013.01); *A61B 2017/2212* (2013.01); *A61B 2017/22034* (2013.01); *B23K 2203/14* (2013.01)

(58) Field of Classification Search
CPC ............. A61B 17/22; A61B 17/22031; A61B 17/12118; A61B 17/320725; A61B 17/221; A61B 19/54; A61M 2025/1052; A61M 2025/1086; A61F 2/013; A61F 2/01; A61F 2/06
See application file for complete search history.

(56) References Cited

U.S. PATENT DOCUMENTS

| | | | |
|---|---|---|---|
| 2003/0055445 A1 | 3/2003 | Evans et al. | |
| 2004/0127920 A1* | 7/2004 | Radisch, Jr. | ... A61B 17/320725 606/159 |

(Continued)

OTHER PUBLICATIONS

United States International Searching Authority; International Search Report for PCT/US2014/033891; issued Aug. 27, 2104; US Patent and Trademark Office; Alexandria, VA; US.

(Continued)

*Primary Examiner* — Victor Nguyen
(74) *Attorney, Agent, or Firm* — Underwood & Associates, LLC

(57) ABSTRACT

In one illustrative embodiment, a thrombectomy device is disclosed. The thrombectomy device includes a treatment portion, comprising a reversibly-expandable framework configured to be deployed from within a microcatheter into a selected vasculature for removing thrombus or embolus. The thrombectomy device further includes a substantially tubular connection member disposed on a proximal end portion of the treatment portion configured to receive a terminal portion of a delivery member for positioning the treatment portion within the vasculature. The framework includes structural features for engaging the thrombus or embolus including one or more of: framework peaks and valleys along a long axis of the treatment portion or a plurality of strut members.

7 Claims, 13 Drawing Sheets

(56) References Cited

U.S. PATENT DOCUMENTS

| | | | |
|---|---|---|---|
| 2010/0137892 A1 | 6/2010 | Krolik et al. | |
| 2011/0125181 A1 | 5/2011 | Brady et al. | |
| 2011/0213403 A1* | 9/2011 | Aboytes ................ | A61F 2/013 606/194 |
| 2011/0319917 A1 | 12/2011 | Ferrera et al. | |

OTHER PUBLICATIONS

United States International Searching Authority; Written Opinion of the International Searching Authority for PCT/US2014/0033891; issued Jul. 6, 2015; US Patent and Trademark Office; Alexandria, VA; US.

Yu, Yongyi Alan; Statement Accompanying Demand for International Preliminary Examination Under PCT Article 31 filed for PCT/US2014/033891; filed on Feb. 12, 2015; Crystal Lake, IL; US.

United States International Preliminary Examination Authority; International Preliminary Report on Patentability for PCT/US2014/033891; issued Jul. 6, 2015; US Patent and Trademark Office; Alexandria, VA; US.

* cited by examiner

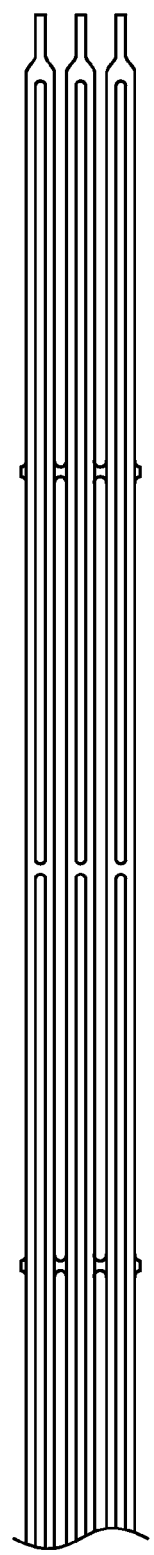
FIG. 15A
FIG. 15B

SYSTEMS AND METHODS FOR RESTORING BLOOD FLOW TO A VESSEL

CROSS REFERENCE TO RELATED APPLICATIONS

This application claims priority to and the benefit of U.S. Provisional Patent Application No. 61/811,689, filed on Apr. 12, 2013, the entire contents of which are incorporated by reference in their entirety as if fully set forth herein.

TECHNICAL FIELD

This disclosure relates to systems and methods for removing blockages, e.g., embolus or thrombus, to restore blood flow in the vasculature of an organism. In particular, thrombectomy devices and methods for their use are disclosed.

BACKGROUND

Acute ischemic stroke is one of the major sources of morbidity and mortality in the industrialized countries. In the USA, approximately 795,000 patients experience a stroke every year. Intravenously administered tissue plasminogen activator (IV tPA) has been shown to improve patient outcome. However, the time window for treatment and the recanalization rate of this approach are limited, and the application of thrombolytic drugs increases the risk of symptomatic intracranial hemorrhage. The success of recanalization, furthermore, depends on the occlusion site.

Mechanical recanalization techniques, i.e., mechanical thrombectomy devices can accelerate the process of recanalization, increase the recanalization rate, and even expand the window of opportunity. Some in-use mechanical thrombectomy devices generally fall into three categories: 1) devices including a filter trap designed and built to collect and remove embolus; 2) a cork-screwed guidewire like device to retrieve embolus; and 3) a stent like device connected to a delivery wire to retrieve embolus.

Some common concerns of physicians who practice angioplasty include: concern that the thrombectomy device may capture an embolus, only to lose hold of it and accidentally deposit it in another area of the neurovasculature; concern that the device may not be able to capture a 'break-off' piece of the embolus, which may migrate further into the neurovasculature; concern that the relatively large device may prevent it from accessing and treating clots in small-diameter vessels; and concern that the devices usually require adhesive joining or bonding between the delivery system and the treatment device. In the latter case, in some instances a concern is that the adhesive bonding may fail, presenting the possibility that the pieces may separate, presenting a serious complication in the procedure.

SUMMARY

In one exemplary aspect, a thrombectomy device is disclosed. The thrombectomy device includes a treatment portion, including a reversibly-expandable framework configured to be deployed from within a microcatheter into a selected vasculature for removing thrombus or embolus. The thrombectomy device further includes a substantially tubular connection member disposed on a proximal end portion of the treatment portion configured to receive a terminal portion of a delivery member for positioning the treatment portion within the vasculature. The framework includes structural features for engaging the thrombus or embolus including at least one of: framework peaks and valleys along a long axis of the treatment portion; and a plurality of V-shaped strut members.

In one exemplary aspect, a device for removing an occlusion within a biological vasculature is described. The device includes a treatment portion, including a substantially cylindrical, self-expandable cage capable of being shifted between a compact delivery configuration and an expanded treatment configuration. The self-expandable cage includes a plurality of interconnected, elongate-rectangular twisted cage struts configured to form a series of substantially diamond-shaped repeat units along a long axis of the cage in the expanded treatment configuration. Corners of the diamond-shaped repeat units are configured to capturingly engage a portion of the occlusion for removal from the biological vasculature. When the cage is in the expanded configuration, proximal and distal end portions of the cage converge inwardly to form substantially close-ended proximal and distal cage end portions respectively. The system further includes a hollow catheter configured for delivering the treatment portion in the delivery configuration to an occlusion site within the biological vasculature.

In one embodiment, the system includes a tubular member disposed on the proximal cage end portion configured to receive a terminal end portion of a control wire for shifting the treatment portion from the compact delivery configuration to the expanded treatment configuration.

In one embodiment, a distal end of one of the cage struts is twisted about its long axis at least 170 degrees relative to a proximal end of the cage strut.

In one embodiment, struts of the treatment portion are configured to produce a repeating wave pattern of strut crests and strut valleys when viewed from a side perspective for maximizing increasing the likelihood of securely engaging the occlusion for removal from the biological vasculature.

In one embodiment, the plurality of interconnected cage struts is configured in a substantially helical pattern between the close-ended proximal and distal cage end portions when the treatment portion is in the expanded configuration. In a related embodiment, the wave pattern has a crest-to-valley distance of between about 0.1 mm and about 8.0 mm. In another related embodiment, the wave pattern has a crest-to-crest distance of between about 0.5 mm and about 20 mm.

In one embodiment, the plurality of interconnected cage struts is coated with a pharmaceutical compound designed to aid in the removal of the occlusion from the biological vasculature.

In one exemplary aspect, a method of producing a device for restoring blood flow to an occluded blood vessel is described. The method includes laser cutting a stock of a biocompatible material in a pattern that, when the material is formed into a substantially cylindrical shape, the material forms a self-expandable treatment portion capable of being shifted between a compact delivery configuration and an expanded treatment configuration. The treatment portion includes a cage formed of a plurality of interconnected cage struts that form a series of substantially diamond-shaped repeat units along a long axis of the cage when the treatment portion is in the expanded treatment configuration. The treatment portion includes a wave-like side profile having crests and valleys formed by the plurality of interconnected cage struts, wherein the wave-like side profile has a crest-to-valley distance of between about 0.1 mm and about 8.0 mm. Corners of the diamond-shaped repeat units are configured to capturingly engage a portion of the occlusion for removal from the blood vessel.

In one embodiment, when the cage is in the expanded configuration, the proximal and distal end portions of the cage converge inwardly to form a tubular connection member having a substantially solid, tube-shaped wall extending along a long axis of the treatment portion. In a related embodiment, the method further includes securing a distal portion of a control wire to the tubular connection member on the proximal end portion of the cage. In a related embodiment, the distal portion of the control wire includes a substantially spherical plug member configured to be urged through the tubular connection member against frictional resistance provided by the interior surface of the substantially solid, tube-shaped wall, until the plug member emerges into the interior of the cage; and welding the plug member to the tubular connection member.

In one embodiment, the proximal and distal end portions comprise between about one and about three of the substantially diamond-shaped repeat units.

In one embodiment, the biocompatible material is Nitinol.

In one embodiment, at least one of the cage struts is twisted at least 180 degrees about its long axis.

In one embodiment, the method further includes attaching a radiopaque material body to the treatment portion. In a related embodiment, the radiopaque material body extends from the proximal to the distal end portion of the treatment portion. In a related embodiment, the radiopaque material body is attached to the distal end portion of the treatment portion.

In one embodiment, the method further includes treating the plurality of interconnecting strut members with an effective dose of a pharmaceutical compound designed to aid in the removal of the occlusion from the blood vessel.

In one embodiment, the method further includes configuring at least one of the strut members with a surface texture for increasing the likelihood of fixedly engaging the strut member to a portion of the occlusion within a biological vasculature.

In one exemplary aspect, a thrombectomy device is disclosed. The device includes an elongate catheter configured to house a deployable basket member that is capable of reversibly shifting from a compact configuration to an expanded configuration as the basket member is urged out of a distal end portion of the catheter. A deployment member spans from a distal end portion of the basket member to a proximal end portion of the catheter so as to be manipulable by a practitioner to control the deployment of the basket member within a vasculature. An arcuate wire member spans opposite sides of a substantially spearhead-shaped wire base, and is configured such that the arcuate wire member and the spearhead-shaped base have a substantially perpendicular relationship when the basket member is in the expanded configuration.

DESCRIPTION OF DRAWINGS

The present embodiments are illustrated by way of the figures of the accompanying drawings which are not necessarily to scale, in which like references indicate similar elements, and in which:

FIGS. 15A and 15B illustrate cut-patterns for making a treatment portion of a thrombectomy device according to one embodiment;

DETAILED DESCRIPTION OF ILLUSTRATIVE EMBODIMENTS

Figure 1:
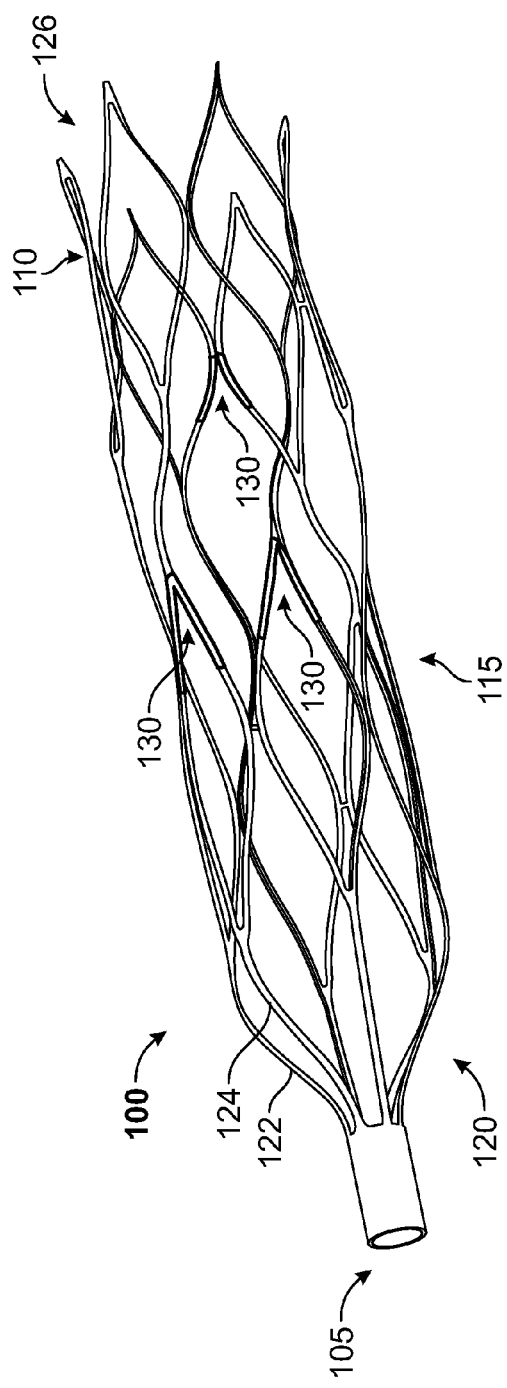
FIG. 1 is a treatment portion of a thrombectomy device according to one embodiment.

In one exemplary aspect, systems and methods for removing thrombus or embolus in a biological vasculature are disclosed to provide the capability of restoring blood flow in an acute ischemic stroke patient. As is well known in the medical arts, timely removal of thrombus or embolus in stroke patients can be a critical survivability factor. In various illustrative embodiments disclosed herein, a mechanical thrombectomy device can include a delivery portion configured to allow selective placement of an expandable treatment portion into a chosen site within a biological vasculature so as to allow the removal or retrieval of an embolus or thrombus.

In one illustrative embodiment described more completely below, the delivery portion can be fabricated from a single wire source or, alternatively, from multiple wires. The expandable treatment portion can be cut, e.g., laser cut from a small section of tubing of appropriate material and subsequently heat treated to form a desired shape; or, in another approach the expandable treatment portion can be cut and formed from braided wires into the configurations as illustrated herein.

In one embodiment, the expandable treatment portion of a thrombectomy device can be configured to improve clot retention during removal of a thrombus or embolus from a biological vasculature. For example, the expandable treatment portion can be configured as a substantially tubular, basket-like framework having peaks and valleys between strut and frame members, as described more fully herein, and can also include at least one tapered, closed end which can facilitate effective and safe removal of thrombus or embolus from a selected vasculature.

In one embodiment, the proximal, distal, or proximal and distal portions of the expandable treatment portion framework can include V-shaped strut joints to assist in engaging a clot within a blood vessel. In various embodiments, one or more bio-agents, pharmaceutical compositions, medicines, or the like can be coated on, attached to, or otherwise incorporated with the treatment portion to assist in dissolving or softening clots for removal. In one embodiment, the treatment portion can include a radiopaque material to assist a practitioner in visualizing the placement of the treatment portion in a selected location within a blood vessel, e.g., using fluoroscopic imaging. In one embodiment, the surface of the expandable treatment portion can be configured to enhance embolus or thrombus affinity by, e.g., coating the surface with a selected affinity substance or configuring the texture of the treatment portion to adhere to the embolus or thrombus by mechanical or chemical methods.

Referring now to the figures, wherein like references indicate similar elements throughout, various embodiments of a thrombectomy device are illustrated. In the discussion that follows, reference is made to one or more "treatment portions" which, for the purpose of this disclosure, generally refer to portions of the thrombectomy device that are configured to engage a thrombus or embolus for the purpose of effecting its removal from a selected portion of an animal (including human) vasculature. Certain figures may illustrate only certain features or parts of the thrombectomy device exclusively for the purpose of highlighting their particular configuration or use. It should be understood, however, that such features or parts can be incorporated into, or assembled as a part of an overall working thrombectomy device capable of being used in a surgical setting by physicians, surgeons, and the like. Similarly, various treatment portion embodiments described herein can be interchangeable with other elements of a thrombectomy device. For example, treatment portions having different dimensions can be reversibly attached to a guidewire, which, in general can be used in manipulating the treatment portion in proximity to thrombus or emboli within a vasculature.

Referring now to FIG. 1, a reversibly-expandable treatment portion (hereinafter "treatment portion") 100 of a thrombectomy device is shown according to one embodiment. In this and other embodiments, the treatment portion 100 is capable of being housed in, and reversibly deployed from a delivery device such as a microcatheter which can be used to deliver the treatment portion to the general area of a thrombus or embolus. In this and other embodiments, the treatment portion is capable of collapsing to a minimum volume so that it can be contained within the delivery device, e.g., a microcatheter (not shown in FIG. 1). In this embodiment, the treatment portion 100 includes a tubular proximal end portion 105 that extends into a framework body 115, and a distal end 110 that, in this embodiment, is an open terminus of the framework body 115. In this and other embodiments, the treatment portion 100 is configured in size and shape so as to be cooperatively used with a microcatheter to deliver the treatment portion 100 to a selected area of a biological vasculature, e.g., the location of a thrombus or embolus. In one embodiment, the proximal end portion 105 can be joined or coupled with a delivery member as described more fully herein.

In this embodiment, a plurality of interconnected struts, e.g., strut 122 and 124, connect the proximal end portion 105 to the framework body 115 as illustrated. In this and other embodiments, the tapered portion 120 can be engaged with a thrombus or embolus during extraction from a vasculature region. For example, the treatment portion 100 can be placed at a selected location near the thrombus or embolus within a vasculature. The treatment portion 100 can be positioned, e.g., by a physician, such that the tapered portion 120 first engages the thrombus or embolus during extraction from the vasculature as described in greater detail below. In this embodiment, the leading edges of the tapered portion 120, e.g., struts 122 and 124 can form engagement surfaces of a radially-expanding cage for engaging a thrombus or embolus perpendicular to the long axis of the treatment portion 100.

In this embodiment, the framework body 115 is formed of a plurality of substantially diamond-shaped framework repeat units, e.g., repeat unit 126, which are formed from interconnected struts; e.g., struts 122, 124, etc. In various embodiments, the number of circumferential repeat units can, without limitation, range from about two to about ten, and the number of linear repeat units, e.g., repeat units substantially aligned along the long axis of the treatment portion 100 can, without limitation, range from about one to about twenty. It should be understood that the number of circumferential or linear repeat units can be selected according to preference, function, or other considerations.

In one embodiment, the cross-sectional diameter of the distal end 110 can be equal to, larger than, or smaller than the cross-sectional diameter of the framework body 115 according to preference, function, or other considerations. For example, the cross-sectional diameter of the distal end 110 can be greater than the cross-sectional diameter at the approximate center of the framework body 115. In such a configuration, the larger-diameter end of the framework body 115 can assist in catching thrombus or embolus fragments that may break off as the treatment portion is engaged with the clot. In such an embodiment, the struts of the framework body 115 at or near the distal end 110 can be configured to minimize the likelihood of damage to the walls of the vasculature from contact. For example, the distal end struts can be smooth, or tapered so as to reduce the likelihood of tearing veins or arteries as the treatment portion is shifted therethrough.

In some embodiments, the size of the repeat units 126 can be homogeneous throughout the treatment portion 110; in other embodiments however, the size, shape, or size and shape of the repeat units 126 can vary. In one embodiment, the size and shape of the various repeat units 126 can vary so as to increase the likelihood of contact and retention of a thrombus or embolus, including parts, fragments, or pieces thereof. In some embodiments, the struts of the framework body 115 can have a selected amount of twist to improve adhesion and engagement with a thrombus or embolus. For example, considering a single diamond repeat unit (e.g., repeat unit 126), in such an embodiment, one or more sides of the diamond repeat unit can include a twisted strut.

In this embodiment, the repeat units of the framework body 115 include V-shaped portions, e.g., V-shaped portions indicated by reference numeral 130 in FIG. 1. These structures can also assist to engage and retain a clot during a thrombectomy procedure and can minimize the likelihood that the clot is disengaged or lost during retrieval.

Figure 2:
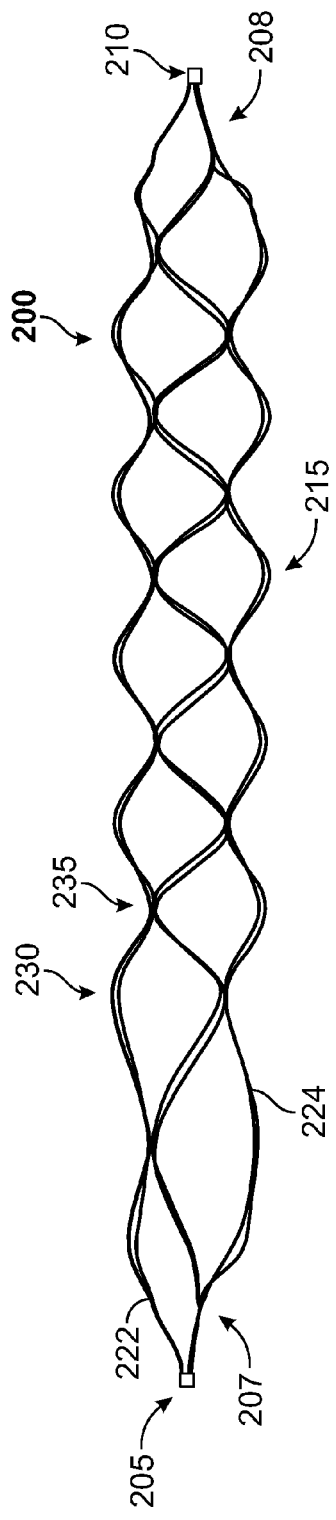
FIG. 2 is a treatment portion of a thrombectomy device according to one embodiment.

Referring now to FIG. 2, an expandable treatment portion 200 is shown according to one embodiment. In this embodiment, the treatment portion 200 includes proximal (205) and distal (210) end portions that each include a tubular portion similar to end portion 105 in FIG. 1, and tapered sections 207, 208, respectively that transition into a framework body 215 formed from struts, e.g., struts 222, 224, etc. In this embodiment, when viewed from a side perspective as illustrated in FIG. 2, the framework body 215 includes crests, e.g., crest 230, and troughs, e.g., trough 235 which are collectively formed by the arrangement of the various struts, as illustrated.

The wave-like pattern of the struts as noticed particularly from a side elevational view can include a repeating crest-to-crest length analogous to a wavelength or wave cycle. In this and other embodiments, the struts of a treatment portion can be configured so as to create a desired wave-like pattern according to preference. In this and other embodiments, the wave-like features of the treatment portion 200 can be selected so as to create a treatment portion that maximizes engagement with an embolus or thrombus. For example, in one embodiment, a treatment portion can be configured to have an exterior wave-like pattern where the crest-to-trough distance is between about 0.1 mm and about 8 mm, and the distance between crests (e.g., the wavelength) is between about 0.5 mm and about 20 mm.

In this and other embodiments, the treatment portion 200 can include one or more twisted strut members having a twisted or torsional configuration about the long axis of the strut that extends a selected length along the long axis of the treatment portion 200. A twisted strut member can be, e.g., strut 222, strut 224, or other strut members of the treatment portion 200. Without wishing to be bound by theory, it is believed that the likelihood of engagement between the treatment portion 200 and a thrombus or embolus is increased due to the complex shape of a twisted strut member compared to a strut member having an untwisted or non-torsional configuration.

In this and other embodiments, a treatment portion can include twisted strut members at desired locations to maximize gripping interaction with a thrombus or embolus. For example, a treatment portion can include one or more twisted strut members as part of a tapered end of the treatment portion, e.g., tapered portion 120 of treatment portion 100 (FIG. 1). In another example, the entire treatment portion can be formed of twisted strut members.

In this embodiment, the closed, tapered ends 205, 210 of the framework body 215 can assist in catching particles that may break off from a main thrombus or embolus body and act as a basket to reduce the likelihood that these particles can be undesirably transported by bodily fluids (such as blood) to other areas of the vasculature. In this embodiment, the framework body 215 includes repeat units similar to that described with respect to FIG. 1. The peaks and valleys formed by the struts and the cell spacing in this embodiment can improve engagement with a clot and reduce the likelihood that the clot will disintegrate as it is being retrieved through the vasculature.

Figure 3:
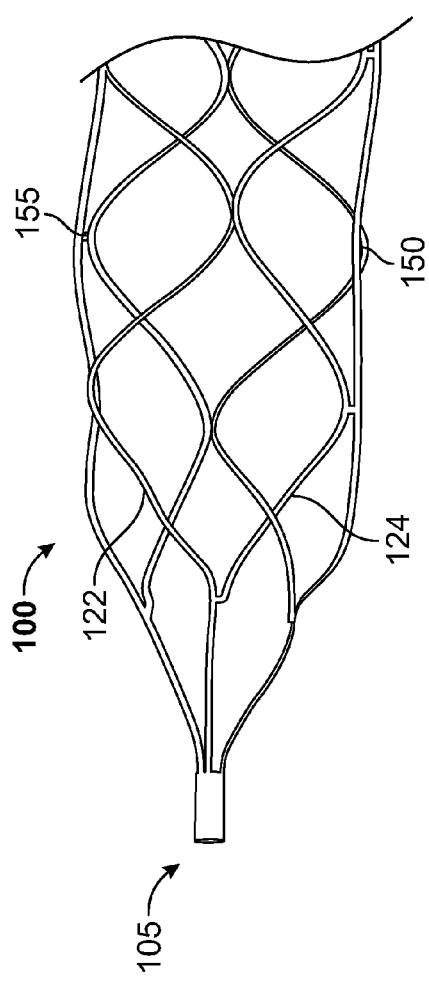
FIG. 3 is a magnified view of the thrombectomy device illustrated in FIG. 2.

FIG. 3 is a magnified view of a proximal end of a framework body, e.g., proximal end portion 105 of framework body 115 according to one embodiment. It should be understood that the view shown in FIG. 3 can be applicable to embodiments other than that described with respect to FIG. 1. FIG. 3 illustrates a twisting pattern of the struts, e.g., struts 122, 124 beginning at each joint where the struts interconnect, e.g., at joints 150 and 155. Such a strut configuration can assist in effective thrombus or embolus removal in that it can provide a varying surface topology throughout the framework body for engaging a thrombus or embolus. In this embodiment, the tubular end segment of the proximal end 105 can be used to join the treatment portion 100 with a delivery portion (not shown in FIG. 3) or used in an assembly of radiopaque elements for visualizing the position of the framework body 100 within a vasculature.

Figure 4:
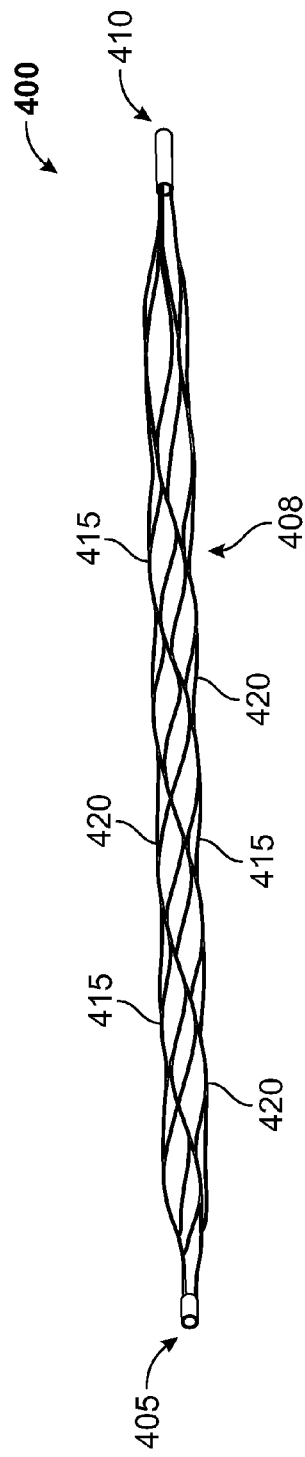
FIG. 4 is a treatment portion of a thrombectomy device according to one embodiment.

FIG. 4 is a perspective view of a treatment portion 400 according to one embodiment. In this embodiment, the framework body 408 includes strut member arranged in a substantially spiraled configuration. For example, elongate strut members 415 and 420 extend from proximal (405) to distal (410) ends of the framework body 408 in a substantially-alternating spiraled arrangement. Such a configuration can facilitate smooth and safe delivery of the treatment portion 400 to the treatment area as well as effective clot engagement and retention. In this embodiment, treatment portion 400 can be used particularly in cases where a patient's vasculature is known to be fragile and thrombus or embolus removal may dictate extra caution.

Figure 5:
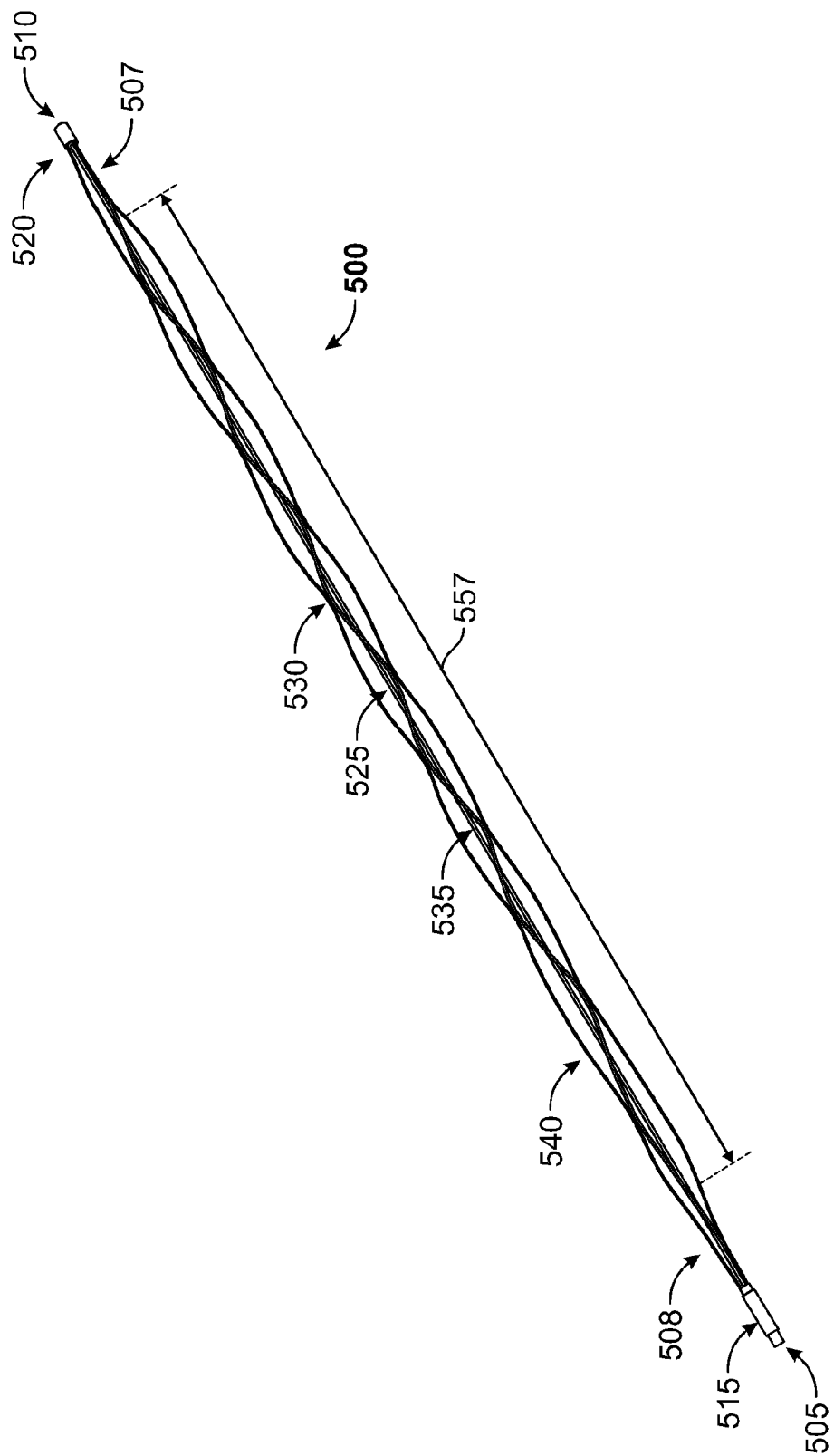
FIG. 5 is a treatment portion of a thrombectomy device according to one embodiment.

Referring now to FIG. 5, a perspective view of an expandable treatment portion 500 is shown according to one embodiment. In this embodiment, the expandable treatment portion 500 can be similar in construction to, e.g., the treatment portion 100 or 200 described with respect to FIG. 1 or 2 respectively, and includes proximal (505) and distal (510) end portions, a distal tapered portion 507, a proximal radiopaque marker 515 and a distal radiopaque marker 520. The treatment portion 500 includes a plurality of twisted struts, e.g., strut 540, configured so as to form valleys 525 and peaks 530 along the long axis of the treatment portion. In this embodiment, the treatment portion 500 includes a marker wire 535 spanning proximal and distal end portions 505, 510 respectively for improved radiopacity. Treatment portions having radiopaque markers can be incorporated into any treatment portion embodiment described herein, including equivalents and modified versions thereof.

Figure 6:
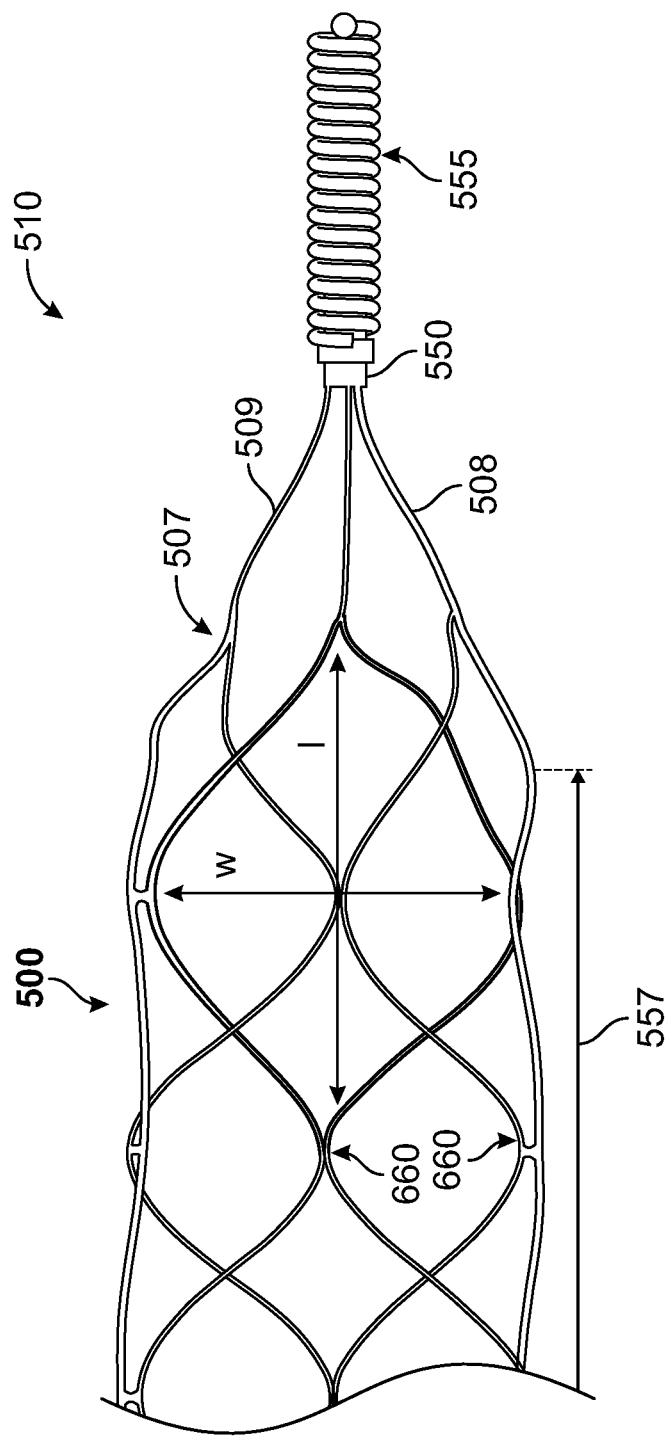
FIG. 6 is a treatment portion of a thrombectomy device having a non-traumatic tip according to one embodiment.

FIG. 6 is a magnified view of the distal portion 510 of the treatment portion 500 in FIG. 5, according to one embodiment. In this embodiment, the strut members of the treatment portion 500, e.g., strut members 508, 509 extend from a tubular end member 550 in a gradually radially-expanding configuration to the elongate, substantially tubular-shaped framework body 557. In some embodiments, the strut members 508, 509 may be independent strut members that span the end member 550 and the framework body 557; in other embodiments, the configuration and orientation of the strut members 508, 509 can gradually transition from a tapered configuration in the tapered portion 507 to a substantially un-tapered configuration as part of the framework body 557. In some embodiments, the struts that together form the framework body 557 can be twisted, e.g., strut member 660. As with other embodiments, tapered strut members can assist in clot removal both through providing a complex surface with which to engage a clot, and in retaining clot fragments that may break off during clot removal or transportation throughout the vasculature. A trauma-reducing tip 555, formed in this example of a spiraled radiopaque material can be used for navigating and positioning the treatment portion by a practitioner. In this embodiment, the device body, e.g., the tubular-shaped framework 557 in this embodiment includes a plurality of repeat units as described heretofore, e.g., with respect to FIG. 1. In this and other embodiments, the cell width (denoted w in FIG. 6) can vary from about 1.5 mm to about 10 mm, although the cell width can be configured to any desired value; in this and other embodiments, the cell length (denoted l in FIG. 6) can vary from about 1.5 mm to about 12 mm, although the cell length can similarly be configured to any desired length value.

Figure 7:
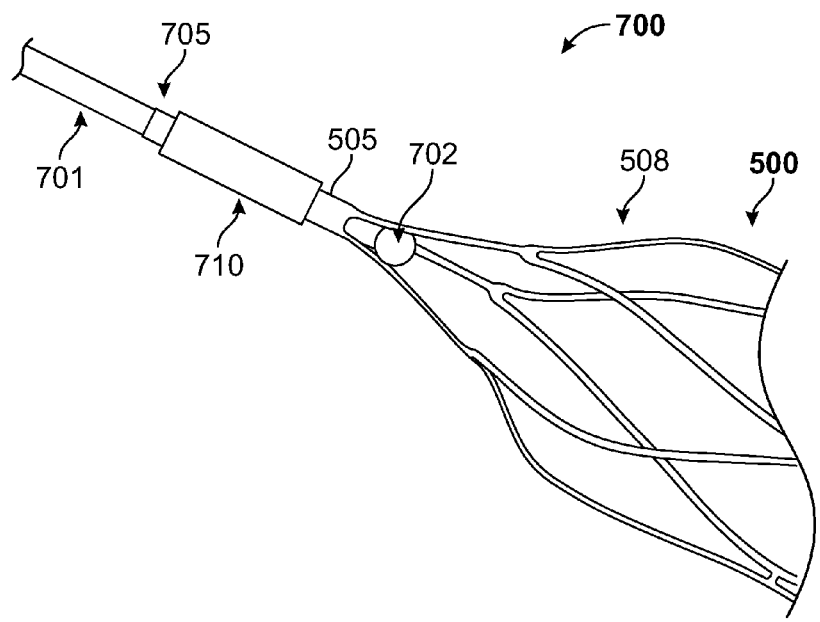
FIG. 7 illustrates connectivity between a treatment portion and a delivery wire in a thrombectomy device according to one embodiment.

Referring now to FIG. 7, a distal portion of a thrombectomy device 700 is illustrated according to one embodiment. In this embodiment, the device 700 includes a treatment portion as described heretofore, e.g., treatment portion 500 as described with respect to FIG. 5, in cooperative assembly with a distal portion of a delivery wire. In this example, reference to treatment portion 500 from FIG. 5 is made, however, it will be understood that other treatment portion embodiments can be substituted in the description that follows.

In this embodiment, an elongate delivery wire 701 includes a bulbous terminal portion 702 configured to prevent the treatment portion 500 from being removed from the delivery wire 701 under normal surgical operating conditions. For example, the treatment portion can be configured to not disengage from the delivery wire 701 as the treatment portion is being used to extract a thrombus or embolus. The bulbous portion 702 can be formed on the tip of the delivery wire by, e.g., thermal heating from a laser after the terminal end of the delivery wire 701 has been advanced through the tubular proximal end 505 of the treatment portion. In one non-limiting approach, a thrombectomy device 700 can be assembled by sliding the treatment portion 500 onto the delivery wire 701 until it reaches a step portion 705 positioned at a selected distance from the terminal portion of the delivery wire 701. The terminal portion of the delivery wire can then be heated to form the bulbous portion as described and to weld the treatment portion 500 to the delivery wire 701. In other embodiments, the treatment portion 500 can be secured to the delivery wire by adhesives or glue. In yet another embodiment, a piece of radiopaque material can be welded onto the distal end of the delivery wire 701 to form a larger profile at the distal end and subsequently mechanically lock the delivery wire in position. A proximal radiopaque marker 710 such as a marker band, marker coil, or radiopaque cover or coating can be assembled and applied to the distal end of the delivery wire as illustrated.

Figure 8:
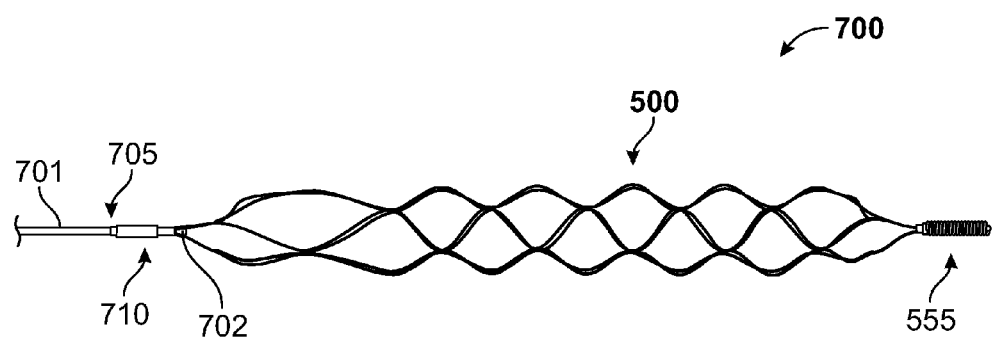
FIG. 8 is a thrombectomy device according to one embodiment.

Combining elements from multiple embodiments described herein, FIG. 8 shows a side elevational view of a portion of the assembled thrombectomy system 700 according to one embodiment, including the distal end of the delivery wire 701, proximal maker 710, expandable treatment portion 500, and distal marker/non-traumatic tip 555.

Figure 9:
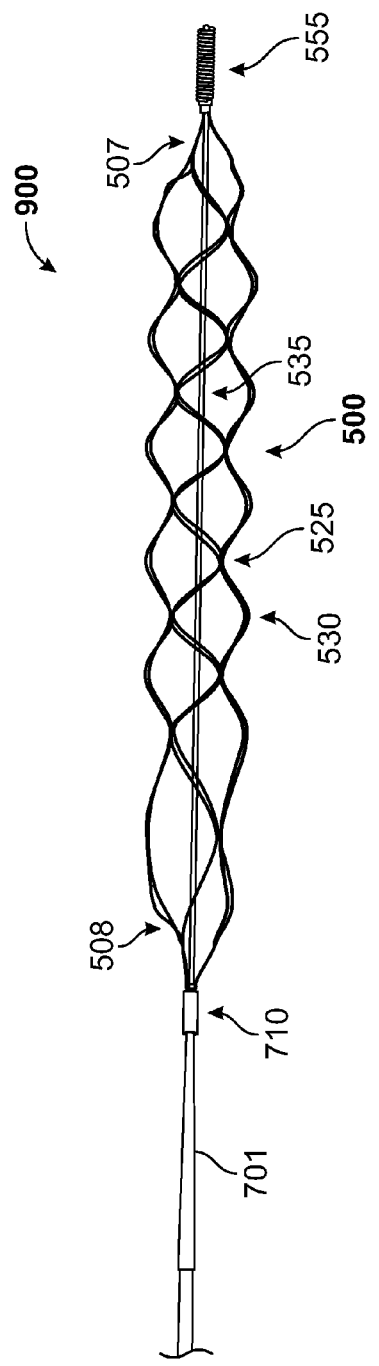
FIG. 9 is a thrombectomy device including a marker wire according to one embodiment.

FIG. 9 shows a side elevational view of an exemplary thrombectomy device 900 including various components as described herein, including a marker wire 535 that spans the length of the treatment portion 500 for full length visualization using radiographic techniques, for example; an expandable treatment portion 500, including peaks 530 and valleys 525 thereof; proximal (508) and distal (507) tapered portions; and a delivery wire 701. In this embodiment, the delivery wire 701 includes a taper in the proximal delivery portion to provide a connection between the delivery wire 701 and the treatment portion 500 having a desired amount of stiffness.

Figure 10:
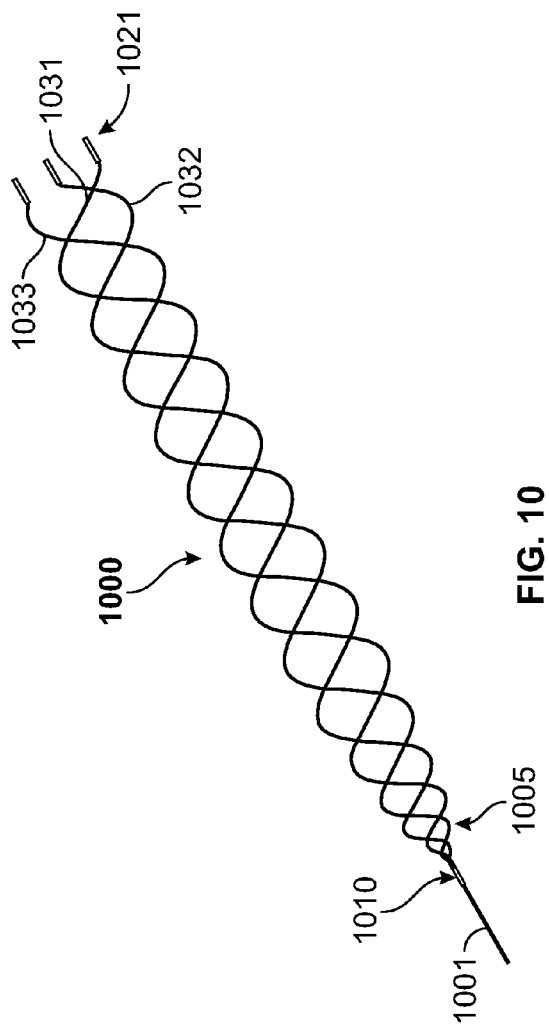
FIG. 10 is a thrombectomy device according to one embodiment.

Referring now to FIG. 10, a braided, reversibly-expandable treatment portion 1000 is shown according to one embodiment. The treatment portion 1000 can be attached to, e.g., a delivery wire 1001 as described herein, and used as part of a thrombectomy device. The proximal end 1005 of the elongated delivery portion 1001 can be fabricated from single wire or multiple wires. If the treatment portion is fabricated from multiple wires, the wires can be the same wires to form the distal expandable portion 1000 of the device system. In this embodiment, the multiple wires 1031, 1032, 1033 at the proximal delivery portion can be twisted together tightly to form a small profile for easy delivery. The stiffness can vary from the proximal delivery portion across the whole treatment portion; in other words, the treatment portion can have a first stiffness at the proximal end, and a second, different stiffness at the distal end 1020.

A radiopaque marker 1010 can be attached to any part of the treatment portion or delivery wire to aid a practitioner in positioning within a vasculature; in this embodiment, the radiopaque marker 1010 is attached to a distal portion of the delivery wire 1001. One or more wires in the device can be made from radiopaque material. In this embodiment, a radiopaque marker, e.g., marker 1021 is attached to each terminus of wire, as illustrated. The distal end of the treatment portion can be open (with or without struts in the lumen) and can have different diameter than the main body with either a flare or taper.

Figure 11:
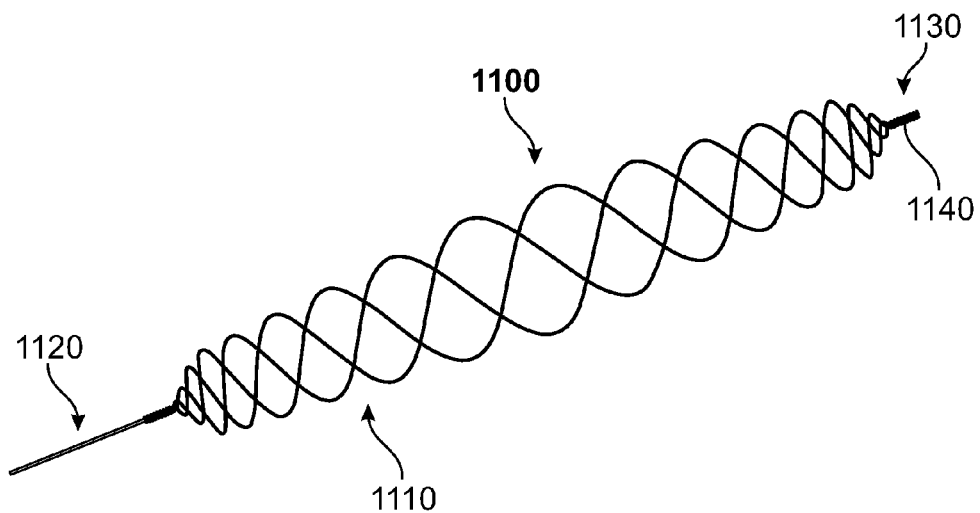
FIG. 11 is a thrombectomy device according to one embodiment.
Figure 12:
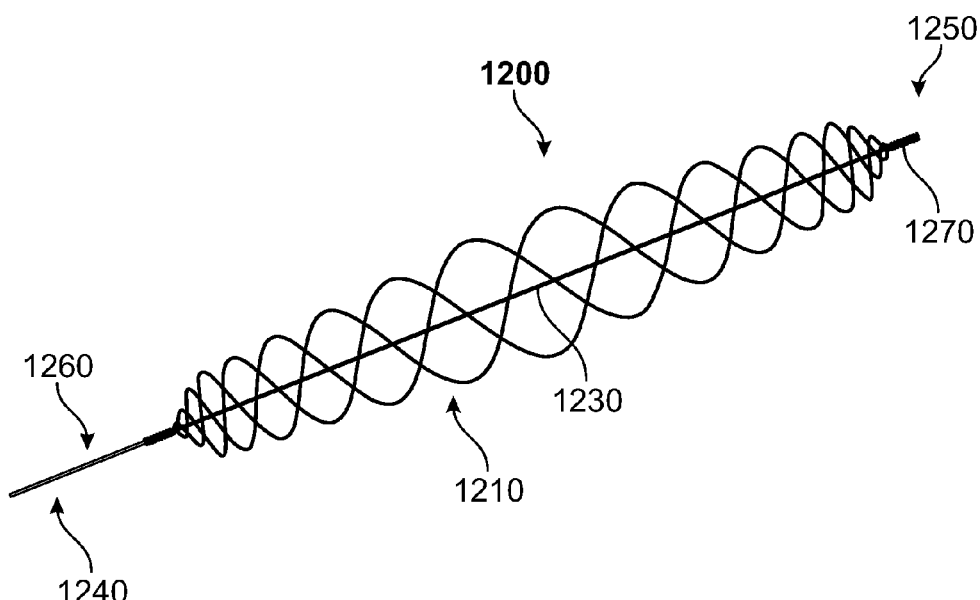
FIG. 12 is a thrombectomy device according to one embodiment.
Figure 13:
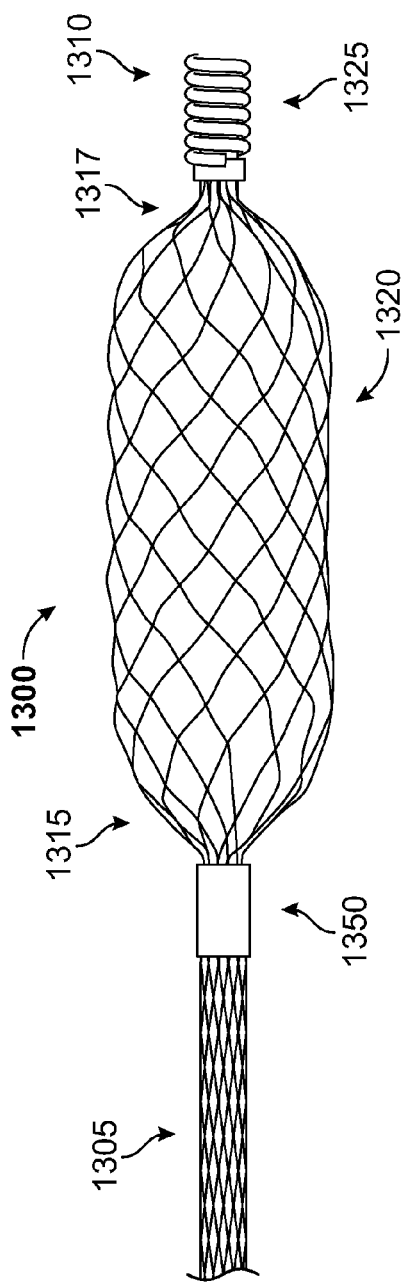
FIG. 13 is a thrombectomy device formed from braided wire, according to one embodiment.

FIGS. 11, 12, and 13 illustrate various alternative treatment portion embodiments of a thrombectomy system as generally described herein. For example, FIG. 11 shows a side-elevational view of a thrombectomy system 1100 with a braided expandable portion 1110 according to one embodiment. The proximal elongated delivery portion 1120 can be fabricated from single wire or multiple wires. If multiple wires are used, the wires can be the same wires that form the distal expandable portion of the system 1100. The distal end 1130 of the expandable portion 1100 can have taper and soft tip with a radiopaque marker 1140 if desired. In this embodiment, the proximal delivery portion has a smaller diameter while the expandable treatment portion has a larger diameter, although other configurations can be used.

FIG. 12 shows a side-elevational view of a thrombectomy system 1200 according to one embodiment, which has a braided expandable portion 1210 with a marker wire 1230 that spans proximal (1240) and distal (1250) end portions. The proximal elongate delivery portion 1260 can be made from, e.g., single wire or multiple wires. If multiple wires are used, the wires can be the same wires with that form distal expandable portion of the system 1200. The distal end 1250 of the expandable portion can have a taper and soft tip with a radiopaque marker 1270 if desired.

FIG. 13 shows a side-elevational view of a portion of a thrombectomy system 1300 system having a braided expandable portion 1320 according to one embodiment. In this embodiment, a proximal elongated delivery portion 1305 can be made from, e.g., single wire or multiple wires. If multiple wires are used, the wires can be the same wires to form the expandable portion 1320 of the system. The expandable portion 1320 can have proximal (1315) and distal (1317) taper portions and a soft-tip radiopaque marker 1325 if desired. In this embodiment, a lumen is formed in the proximal delivery portion 1305 as illustrated; heat shrink tubing 1350 or a polymer cover can be used to form the interface between the lumen 1305 and the expandable portion 1320. In this embodiment, the proximal delivery portion can have variable stiffness along the length.

Figure 14:
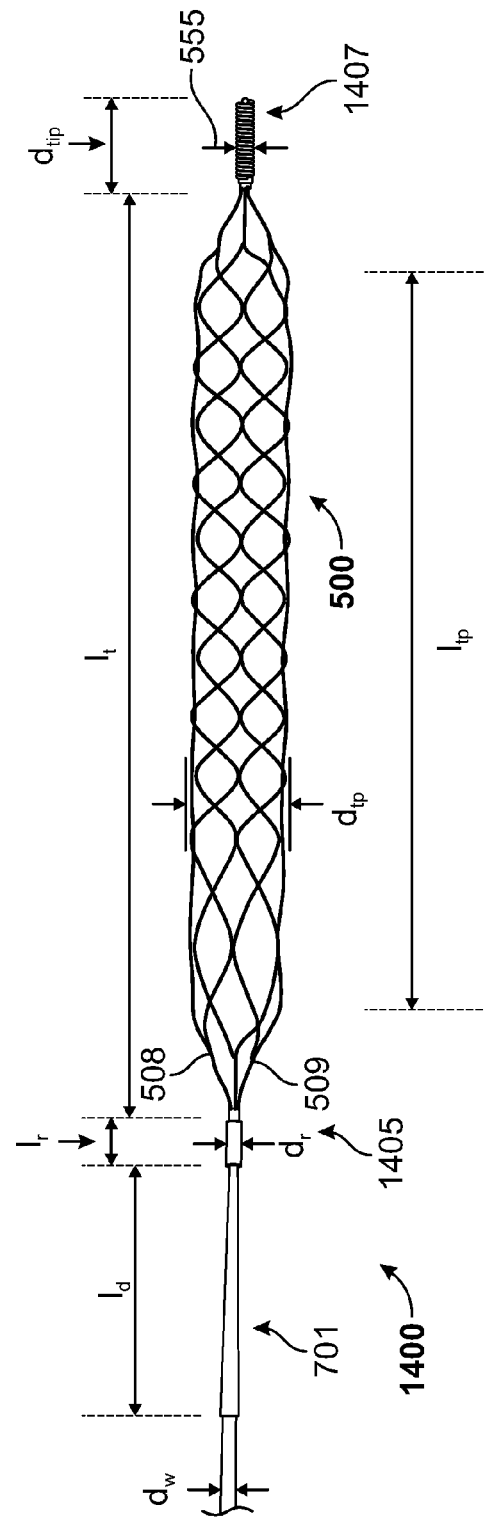
FIG. 14 is a thrombectomy device according to one embodiment.

Referring now to FIG. 14, a portion of a thrombectomy device 1400 incorporating various elements from embodiments described herein is shown according to one embodiment. In this embodiment, the treatment portion can be made from a wire providing variable stiffness along its length. In this embodiment, the diameter of the expandable treatment portion is substantially the same across its length; however, the diameter can vary along the length in alternative embodiments. In this embodiment, the distal end 1407 of the expandable treatment portion is be tapered to increase the likelihood of retaining any fragments of a thrombus or embolus that break off during extraction from a vasculature site. In this embodiment, a soft, non-traumatic tip made from radiopaque material 1410 is attached to the distal end 1407 of the delivery portion 1405. In this embodiment, the device treatment portion 500 can be fabricated from Nitinol super elastic material, Nitinol shape memory alloy tubing, or any other biocompatible material that exhibits super elastic or shape memory properties. In one embodiment, the treatment portion 500 can be fabricated using laser cutting, mechanical machining, chemical machining, electrochemical machining, EDM, or other methods. The delivery wire 1405 can be made either from single wire or multiple wires components as described herein, for example. In one embodiment, the delivery wire

701 can have variable stiffness along its length to facilitate smooth delivery and easy retrieval of the device.

A radiopaque marker 555 (marker band, marker coil, marker wire, marker coating, or other marker) can be attached at the proximal 1405 and distal 1407 ends of the treatment portion 500 to help with device positioning. In this embodiment, the treatment portion is configured with a plurality of peaks and valleys as heretofore described to improve clot adhesion and retrieval. For example, the peak and valleys along the length of the treatment portion 500 can cooperatively engage and retain the clot volume and reduce the amount of force necessary to remove the clot from a vasculature, e.g., to prevent the clot from breaking. In this embodiment, the strut(s) of the device treatment portion e.g., struts 508 and 509 can be arranged at an angle from about 5 degrees to about 175 degrees from the longitudinal axis of the device. In this embodiment, the plurality of struts that form the treatment portion 500 can be twisted to improve clot affinity and retention during a thrombectomy or embolectomy procedure. In this embodiment, the surfaces of the plurality of struts can be modified by chemical or physical methods, e.g., mechanical surface roughness modification, chemical etching, PVD, CVD, surface coating, micro pinning, or other techniques for improved clot retention and retrieval.

In this and other embodiments, the dimensions of the system can be chosen and configured according to preference or to meet desired performance characteristics. For example, referring to FIG. 14, the total length $l_t$ of the treatment portion (including the tapered portions) can be varied to accommodate different sizes and shapes of vasculature or target thrombi or emboli; the effective length $l_{tp}$ of the treatment portion 500, the length $l_d$ of the delivery wire, the length $l_r$ and diameter $d_r$ of the radiopaque marker, the diameter of the delivery wire $d_w$, the length of the distal tip $l_{tip}$, the diameter of the treatment portion $d_{tp}$, and any other aspect of the thrombectomy device 1400 can each be independently varied or modified from that described and illustrated herein to provide certain advantages or to meet desired performance characteristics.

In various embodiments, the proximal delivery portion can be formed from, for example, Nitinol wire or stainless steel wire having a diameter between about 0.005 inches and about 0.060 inches, although other materials can be substituted. In some embodiments, the length of wire in a thrombectomy device (e.g., device 1400 in FIG. 14) can vary, e.g., from about 60 em to about 200 cm. In some embodiments, the diameter of the tapered portions, e.g., tapered portion 120 in FIG. 1 can be, e.g., from about 0.005 inches to about 0.055 inches. In various embodiments, the aforedescribed radiopaque markers can be made from, e.g., Pt, Pt—Ir alloy, W, Ta, or other radiopaque materials. In some embodiments, the length of the tapered portion, e.g., tapered portion 120 in FIG. 1 can be, e.g., from about 10 mm to about 150 cm. In various embodiments, a proximal marker can be in the form of, e.g., a marker band, or marker coil, or a polymer extrusion having a loaded radiopaque material. In some embodiments, the length of the radiopaque marker can be, e.g., from about 0.5 mm to about 100 mm. In some embodiments, the diameter of the marker can vary, e.g., from about 0.005 inches to about 0.060 inches. In some embodiments, the treatment portion can be from about 8 mm to about 80 mm. In some embodiments, the diameter of the treatment portion can be, e.g., from about 1.5 mm to about 12 mm. In some embodiments, the struts have a strut thickness of between about 20 μm and about 200 μm.

Referring now to FIGS. 15A and 15B, laser cut patterns for producing a treatment portion of the type described herein are illustrated according to one embodiment. In this embodiment, which can be a manufacturing method, the treatment portion can, after being laser cut, be heat treated and expanded to its final diameter as is known in the art; a surface treatment can optionally be applied thereafter to provide desired strut surface characteristics for engaging and retaining clots of various type within a vasculature. In one embodiment, a mandrel can be used to apply a desired amount of twist to the struts to form a treatment portion framework having twisted struts as described herein, e.g., treatment portion 200 described with respect to FIG. 2. The laser cut patterns shown in FIGS. 15A and 15B can produce a treatment portion as illustrated in FIG. 14.

Referring now to FIGS. 16A-16D, a method for using a thrombectomy device as described herein is disclosed according to one non-limiting embodiment. It will be understood that the following example is one of many methods that may be used to treat patients having a thrombus or embolus, e.g., a stroke patient, and the chosen treatment can be selected and/or modified by a physician as he deems necessary.

Figure 16A:
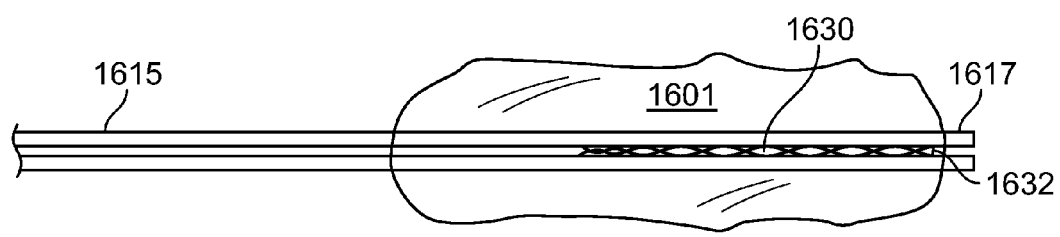
FIGS. 16A-16D illustrate a method for using a thrombectomy device to remove a thrombus from a blood vessel according to one embodiment.

First, referring to FIG. 16A, a suitable guidewire (not shown in FIGS. 16A-16D) can be advanced through the vasculature to the location of the thrombus 1601. The guidewire can be inserted through the thrombus 1601 as is generally known in the art. A microcatheter 1615 can be advanced along the guidewire until it has extended through the thrombus 1601 a desired amount, as illustrated. In some methods, fluoroscopic imaging can aid the practitioner in the proper placement of the guidewire and the microcatheter 1615. Next, while maintaining the position of the microcatheter 1615, the guidewire can be withdrawn through the microcatheter 1615.

A treatment portion 1630 of a thrombectomy device, such as any of the treatment portions described herein, can be advanced through the microcatheter 1615 until its distal tip 1632 reaches approximately the distal end 1617 of the microcatheter 1615. As generally described herein, the treatment portion can include a delivery wire, e.g., delivery wire 701 coupled to the treatment portion, e.g., treatment portion 100. As previously disclosed, the treatment portion can include markers of any suitable type which can aid the practitioner in proper placement relative to the thrombus 1601. In one approach, the distal end 1632 of the treatment portion 1630 can be advanced beyond the thrombus 1601 to ensure that an adequate amount of the treatment portion engages the clot. In another approach, the distal end of the treatment portion 1630 can be positioned so that when the microcatheter 1615 is retracted, the treatment portion 1630 expands substantially within the thrombus 1601 as illustrated in FIGS. 16A-16D. In yet another approach, the treatment portion can be advanced past the thrombus so that the proximal end 1633 of the treatment portion engages the thrombus as it is retracted from the vasculature, e.g., in the direction of the arrow in FIGS. 16B-16D.

Figure 16B:
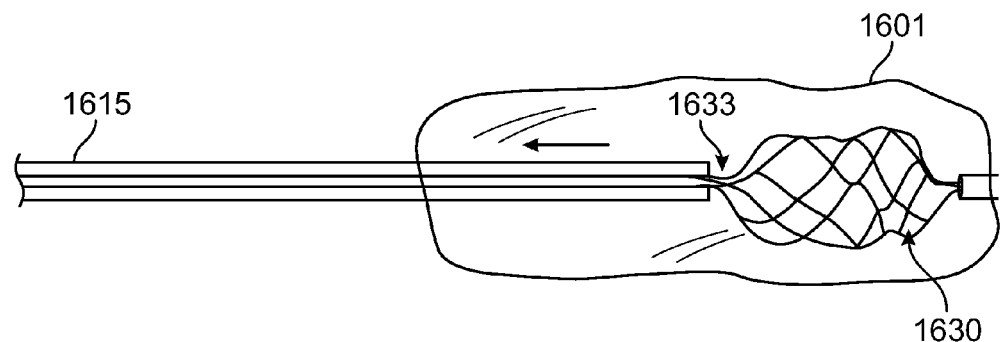
Figure 16C:
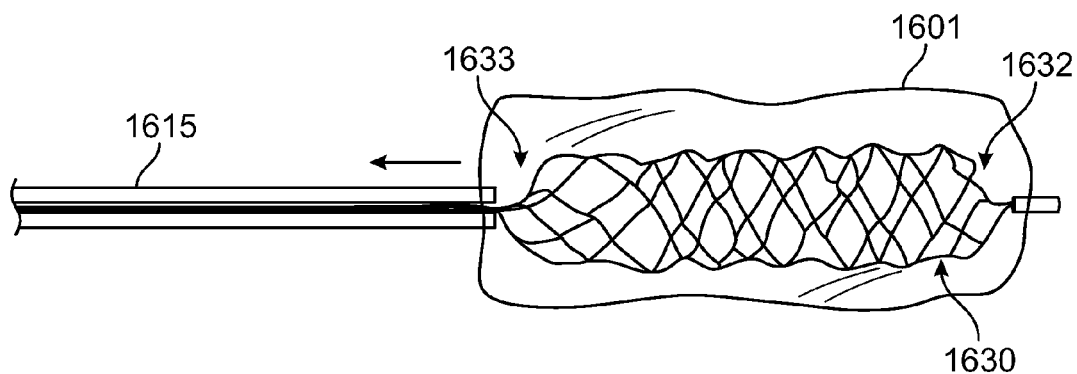
Figure 16D:
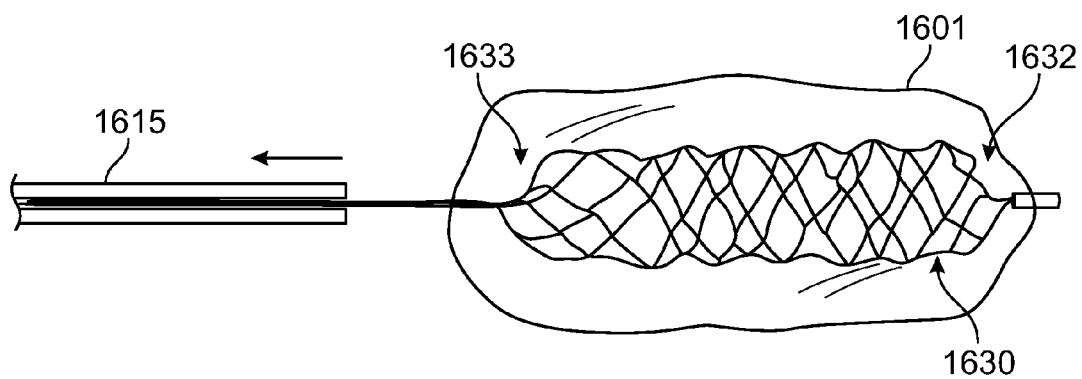

Next, referring to FIGS. 16B-D, the practitioner can stabilize the position of the treatment portion 1630 via the delivery wire while retracting the microcatheter 1615. In this embodiment, as the microcatheter 1615 is withdrawn, the treatment portion of the thrombectomy device expands, thus engaging the thrombus 1601 in and throughout the framework of the treatment portion. Finally, the treatment portion can be withdrawn together with the microcatheter from the vasculature and out of the body, carrying the thrombus with it.

Figure 17A:
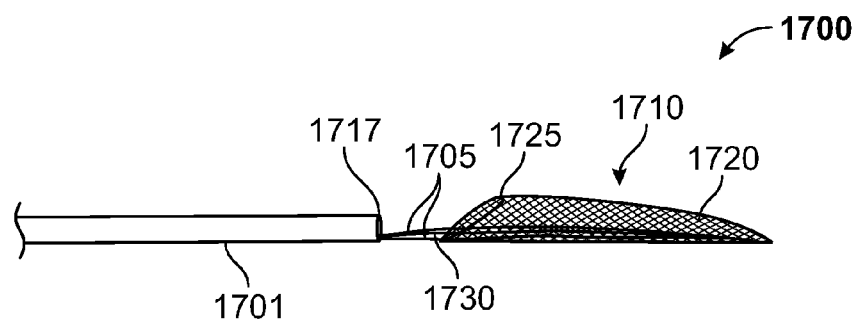
FIGS. 17A-17G illustrate a thrombectomy device according to one embodiment and a method of its use.
Figure 17B:
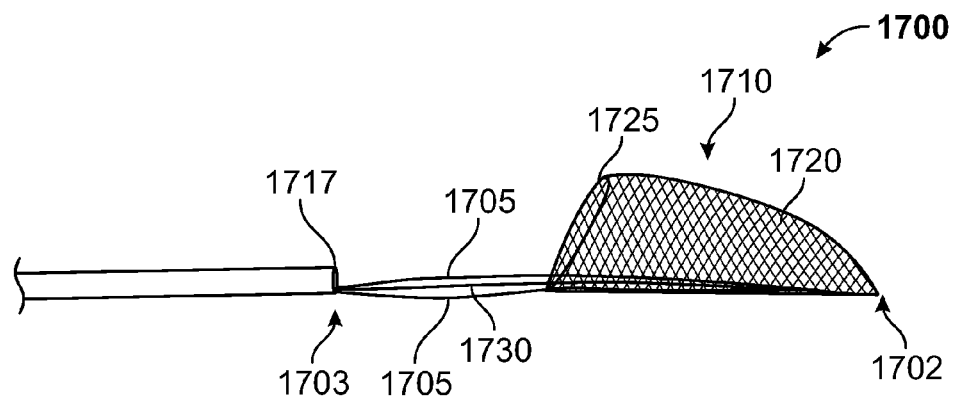

Referring now to FIGS. 17A and 17B, a thrombectomy device 1700 is illustrated according to one non-limiting embodiment. FIG. 17A illustrates a reversibly-deployable and expandable basket member 1710 of the thrombectomy device 1700 in a partially-expanded configuration, and FIG. 17B illustrates the basket member 1710 in a fully-expanded configuration. In this embodiment, the device 1700 includes a delivery catheter 1701 which is configured so as to fit, and be maneuverable within a selected vasculature. It should be understood that the catheter 1701 and the other components of the device 1700 can be configured to accommodate use in a variety of vasculature shapes and sizes. Similarly, the catheter 1702 can be flexible so as to allow propagation of the distal tip 1717 to a selected region within a vasculature.

In this embodiment, the basket member 1710 can be reversibly deployed from within the catheter 1701 by shifting a wire deployment member 1730 which is coupled to the basket member 1710 at a distal end portion 1702. In this embodiment, the deployment member 1730 spans from the distal end portion 1702 to a proximal end portion of the catheter (not illustrated) and is configured to be manipulable by a practitioner to control deployment of the basket member 1710 from the distal end of the catheter 1717, e.g., as illustrated in the series of illustrations in FIGS. 17C-17G.

In this embodiment, a reversibly-expandable cage portion 1720 of the basket member 1710 can expand between compact and extended configurations. In this embodiment, a compact configuration can be one in which the cage portion 1720 is housed within the catheter 1701 and correspondingly occupies a minimum volume. An expanded configuration can be one in which the cage portion 1720 is extended outside of the catheter 1701 and expands such that the opening of the basket, defined substantially by arcuate wire member 1725, fills the cross-sectional diameter of the blood vessel as illustrated in FIGS. 17C-17G.

In this embodiment, the cage portion 1720 extends from the arcuate wire member 1725 toward the distal end portion 1702 as illustrated. In this embodiment, the base of the basket 1710 is defined by wire member 1705. When the basket member 1710 is in an extended configuration, wire member 1705 assumes a spear point shape, where the wire 1705 comes to a point at the distal end 1702 along a centerline of the elongate axis, e.g., parallel with deployment member 1730.

Figure 17C:
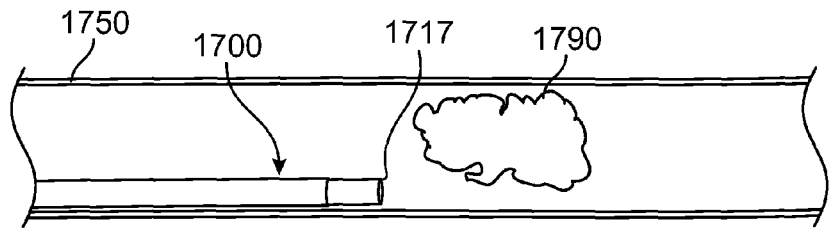
Figure 17D:
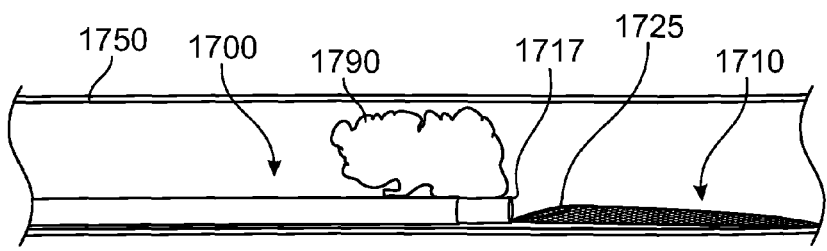

Device 1700 can be particularly beneficial for removing thrombus or emboli while reducing the likelihood of releasing fragments that can later become nuclei for the formation of downstream clots. Referring now to the FIGS. 17C-17G, a method of using the device 1700 is illustrated according to one embodiment. In FIG. 17C, a distal portion 1717 of the delivery catheter 1701 is advanced in an artery 1750, e.g., under the control of a physician, to an area substantially adjacent to an arterial thrombus or embolus 1790. Next, referring to FIG. 17D, the basket member 1710 can be advanced under, around, or through the thrombus or embolus 1790 by controlled shifting of the deployment member 1730, again, for example, under the direction or control of a physician.

Figure 17E:
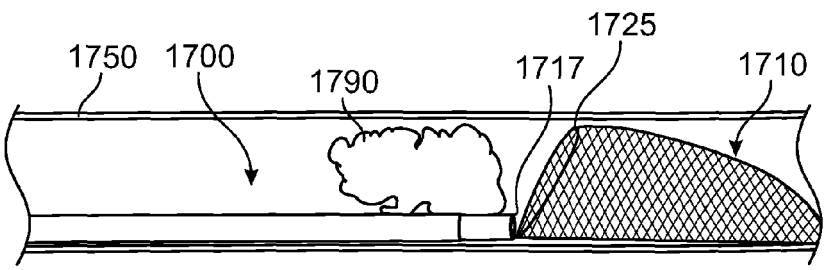
Figure 17F:
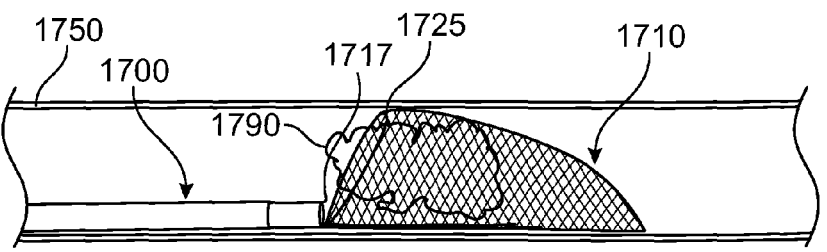
Figure 17G:
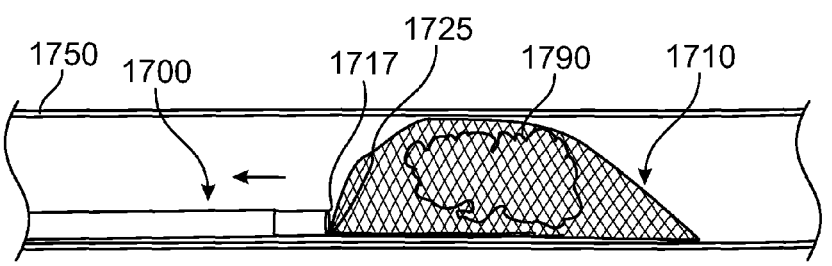

Next, referring to FIG. 17E, the cage portion 1720 can be expanded such that arcuate wire member 1725 has a diameter suitable to surround all, or most of the thrombus 1790. In general, the cage portion 1720 can be controllably expanded by a practitioner. In some cases, the cage portion 1720 can be expanded such that the arcuate wire member 1725 confronts the inner wall of the artery substantially along its arcuate length. In a preferred method, radiographic techniques can be used to verify that the distal end 1717 and the cage portion 1720 pass the thrombus 1790 to ensure full capture prior to removal. Once the cage portion 1720 is expanded, the delivery catheter 1701 and the basket member 1710 can be synchronously shifted in a direction to withdraw the device 1700 from the patient (FIG. 17F). As the catheter 1701 is being withdrawn, the basket member 1710 can be shifted to a closed configuration, illustrated in FIG. 17G to fully capture the thrombus 1790 within the basket member 1710. In one embodiment, the catheter can be configured so as to allow the basket member 1710 to be drawn therewithin, including the thrombus 1790, while it is being removed from the patient.

In this embodiment, the closed portion of the basket member 1710 at the distal end portion 1702 can reduce the likelihood of the thrombus or embolus 'escaping' during removal, and similarly increase the likelihood of capturing any thrombus or embolus fragments that may break off of the main body during removal.

A number of illustrative embodiments have been described. Nevertheless, it will be understood that various modifications may be made without departing from the spirit and scope of the various embodiments presented herein. For example, a thrombectomy device as described herein can include other components and features that enable the treatment portion of the device to be used as generally described herein. For example, certain controls configured for use by a physician to guide the treatment portion can be incorporated. While not illustrated in the figures, it should be understood that the various treatment portions and delivery wires attached thereto can be controlled by hand, robot, or other means for positioning and extracting clots from vasculature. Fiber optic visualization components for feeding the treatment portion to its intended location or for assisting in clot removal can similarly be incorporated into a thrombectomy device. In one example, pharmaceutical compounds, including clot-reducing or softening compounds can be introduced to a clot site through the delivery wire. Any of the device embodiments described herein, including modifications thereof, can be appropriately sized so as to be capable of being loaded into a delivery catheter (for example, a microcatheter), and delivered to a target location in a vessel to retrieve a clot. A device of the type described herein can have a surface treatment on various portions thereof to improve performance or to satisfy other device requirements for use. For example, any portion of a thrombectomy device can be coated or covered by a biocompatible material to provide lubrication entirely or partially. The surface of the distal treatment portion can have a positive or negative charge for improved clot adhesion. The surface of the distal treatment portion can also be mechanically or chemically treated to have a rough surface for improved clot adhesion. The rough surface can be achieved by, e.g., 1) providing a porous surface coating or layer; 2) microblasting or micropinning one or more surfaces of the thrombectomy device; or 3) providing an irregular strut geometry or arrangement, for example, providing twisted struts or struts with varying angles. Accordingly, other embodiments are within the scope of the following claims.

What is claimed is:

1. A method of producing a device for restoring blood flow to an occluded blood vessel, comprising:

cutting a stock of a biocompatible material in a pattern that, when said material is formed into a substantially cylindrical shape, said material forms a self-expandable treatment portion capable of being shifted between a compact delivery configuration and an expanded treatment configuration;

wherein said self-expandable treatment portion comprises a cage formed of a plurality of interconnected cage struts that form a series of substantially diamond-shaped repeat units along a long axis of said cage when said self-expandable treatment portion is in said expanded treatment configuration;

wherein said self-expandable treatment portion comprises a wave-like side profile having crests and valleys formed by said plurality of interconnected cage struts, wherein said wave-like side profile has a crest-to-valley distance of between about 0.1 mm and about 8.0 mm;

wherein corners of said diamond-shaped repeat units are configured to capturingly engage a portion of said occlusion for removal from said blood vessel;

wherein, when said cage is in said expanded treatment configuration, a proximal end portion of said cage converges inwardly to form an elongate tubular connection member extending outwardly and substantially coaxially with a long axis of said self-expandable treatment portion;

forming a bulbous terminal portion on a terminal end portion of a delivery wire after said terminal end portion has been advanced through said tubular connection member;

attaching said bulbous terminal portion to said tubular connection member within the interior of said self-expandable treatment portion; and attaching a radiopaque material body proximal to said proximal end portion of said self-expandable treatment portion.

2. The method of claim 1, wherein said proximal and distal end portions comprise between about one and about three of said substantially diamond-shaped repeat units.

3. The method of claim 1, wherein said biocompatible material is Nitinol.

4. The method of claim 1, wherein at least one of said cage struts is twisted at least 180 degrees about its long axis.

5. The method of claim 1, wherein said radiopaque material body extends from said proximal to said distal end portion of said self-expandable treatment portion.

6. The method of claim 1, further comprising treating said plurality of interconnecting strut members with an effective dose of a pharmaceutical compound designed to aid in the removal of said occlusion from said blood vessel.

7. The method of claim 1, further comprising configuring at least one of said strut members with a surface texture for increasing the likelihood of fixedly engaging said strut member to a portion of said occlusion within a biological vasculature.

* * * * *